United States Patent [19]

May

[11] 4,178,642
[45] Dec. 18, 1979

[54] KNEE JOINT STRUCTURE FOR ARTIFICIAL LEGS

[75] Inventor: Denis R. W. May, London, England

[73] Assignee: J. E. Hanger & Company Limited, London, England

[21] Appl. No.: 851,323

[22] Filed: Nov. 14, 1977

[30] Foreign Application Priority Data

Nov. 18, 1976 [GB] United Kingdom ............... 48085/76

[51] Int. Cl.² ............................................. A61F 1/04
[52] U.S. Cl. ......................................................... 3/28
[58] Field of Search ...................... 3/22, 26, 28, 23, 24, 3/25, 29, 27

[56] References Cited

U.S. PATENT DOCUMENTS

| 2,000,066 | 5/1935 | Didier | 3/29 |
| 2,057,534 | 10/1936 | McCann | 3/22 |
| 2,170,580 | 8/1939 | Steele et al. | 3/24 |
| 2,559,446 | 7/1951 | Lucas et al. | 3/28 X |
| 3,309,715 | 3/1967 | Nader et al. | 3/28 X |
| 3,694,823 | 10/1972 | May | 3/29 X |
| 3,823,424 | 7/1974 | May | 3/22 |
| 4,064,569 | 12/1977 | Campbell | 3/26 |

FOREIGN PATENT DOCUMENTS

| 168874 | 9/1951 | Austria | 3/27 |
| 2135352 | 1/1973 | Fed. Rep. of Germany | 3/28 |
| 2239679 | 2/1974 | Fed. Rep. of Germany | 3/22 |
| 1276647 | 6/1972 | United Kingdom | 3/22 |

Primary Examiner—Clifford D. Crowder
Attorney, Agent, or Firm—Pollock, Vande Sande and Priddy

[57] ABSTRACT

An artificial leg of the kind in which the shin portion and the knee portion are shaped from a block of wood or similar solid material, has the knee and shin portions connected by pairs of front and rear links, the effective length of the front links being less than that of the rear links and the connections between the links and the knee and shin portions being positioned so as to form an articulation of which the instantaneous center of rotation lies upon an ascending curve for a predetermined angle of relative rotation between the two portions of the leg from the fully extended position. The resultant joint provides a stable weight support until it has been flexed through the predetermined angle and is thereafter capable of flexure through more than a right angle.

5 Claims, 4 Drawing Figures

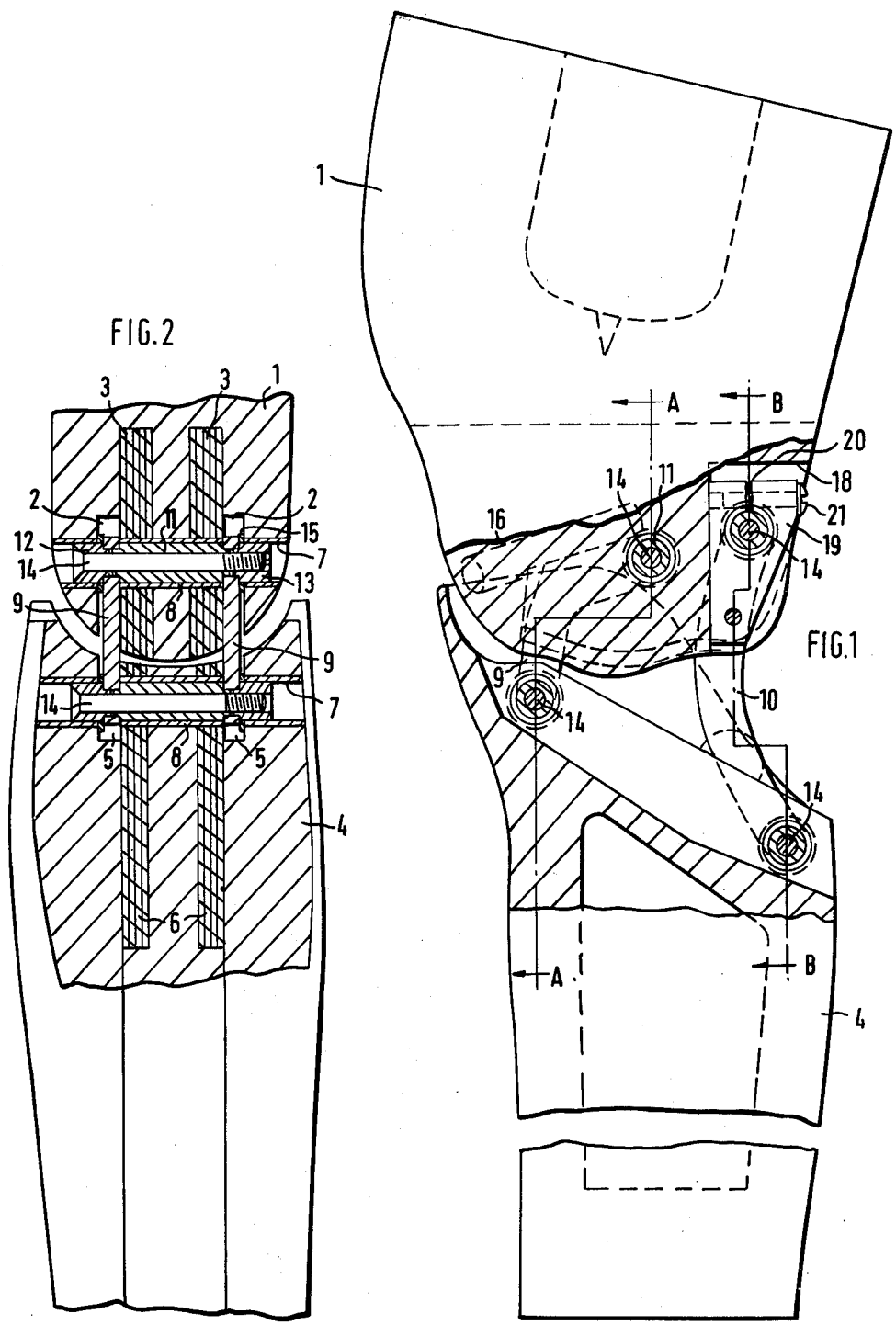

KNEE JOINT STRUCTURE FOR ARTIFICIAL LEGS

BACKGROUND OF THE INVENTION

This invention is concerned with artificial legs of the kind comprising a shin portion and a knee portion both shaped from wood or similar material and particularly to the improvement of the knee joint whereby the shin and knee portions are articulated together.

It is desirable for the knee joint of such legs to provide a stable weight support over a relatively small angle of flexure, say 15 degrees from the extended position and thereafter be capable of easy flexure through more than a right angle to facilitate sitting down and rising from the sitting position.

PRIOR ART

The most relevant prior art known to the inventor is his prior U.S. Pat. No. 3,823,424.

SUMMARY OF THE INVENTION

An artificial leg according to the invention comprises a knee portion and a shin portion both shaped from wood or the like and each formed in their confronting surfaces with a pair of grooves running from front to rear, a pair of front links and a pair of rear links engaged in said grooves, opposite ends of each of said links being pivotable about pivot pins passing through said knee portion and said shin portion, the effective length of said front links being less than that of said rear links and the positioning of the pivot pins being such as to form an articulation of which the instantaneous center of rotation lies upon an ascending curve for a predetermined angle of relative rotation between the two portions of the leg from the fully extended position.

The resultant articulated joint provides a stable weight support until it has been flexed through the predetermined angle from the extended position which may be about 15 degrees. The joint is thereafter capable of flexure through more than a right angle, say 120 degrees to permit a natural sitting posture.

The effort necessary to flex the knee may be controlled by a brake which advantageously comprises a nylon or similar block surrounding one of the pivot pins and adjustably clamped thereabout by a screw.

The front links are preferably cranked so that in the extended position of the leg, they abut against buffer stops at the bottom of the grooves in the knee portion. A buffer stop may be provided on the knee portion between the grooves thereon against which the shin portion abuts when the knee is in the fully flexed position.

BRIEF DESCRIPTION OF THE DRAWINGS

FIG. 1 is a side view partly in section of a knee joint in accordance with the invention;

FIG. 2 is a section on the line A—A of FIG. 1;

Figures 3, 4:
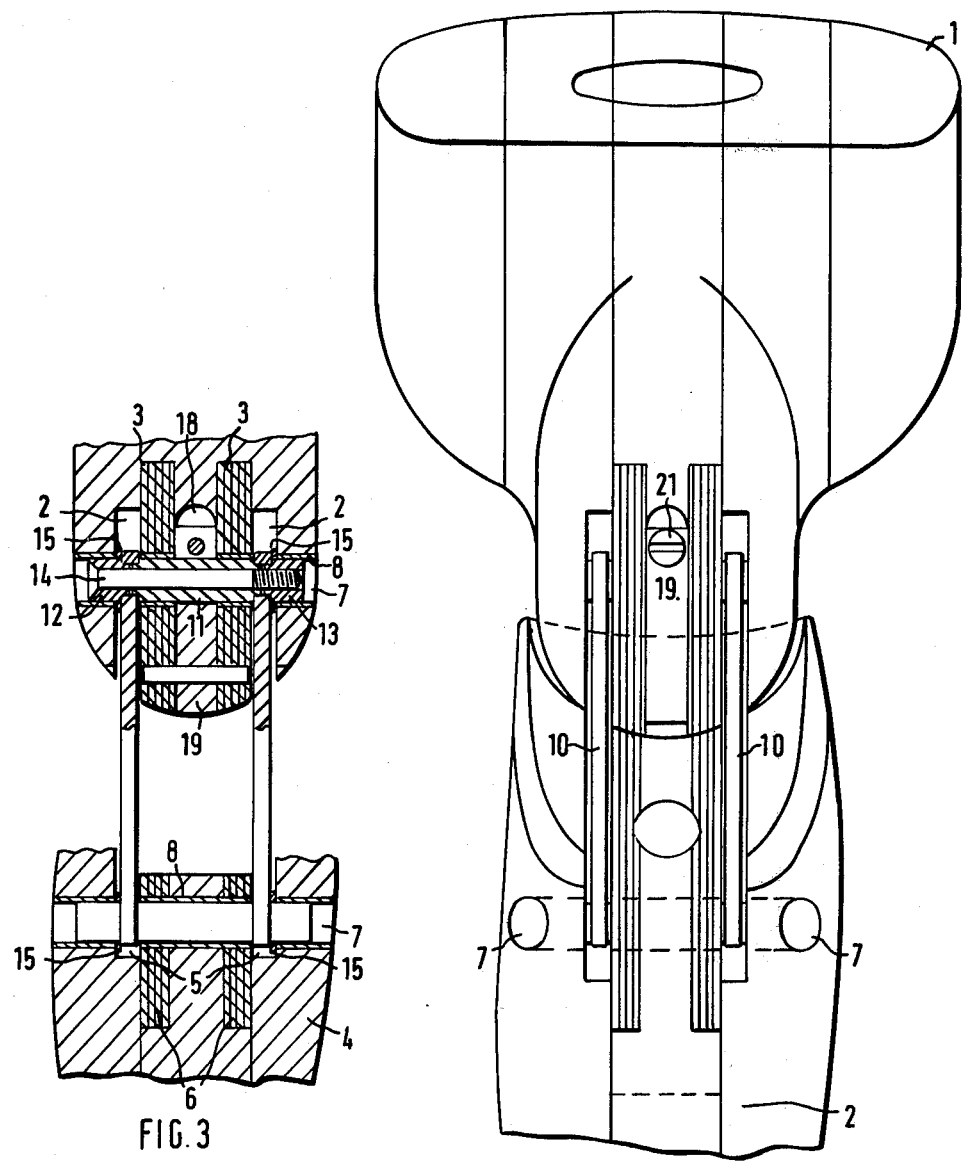
FIG. 3 is a section on the line B—B of FIG. 1.
FIG. 4 is a rear elevation. In the form shown, a knee portion 1 which may be the stump socket for an amputee's upper leg stump, is shaped from a block of laminated wood. In the bottom of this portion are formed two parallel grooves 2, 2 running from front to rear of the leg. Plates 3 of synthetic resin bonded plywood are inset in the knee portion and define the inner sides of the grooves 2.

The shin portion 4 is similarly shaped from a laminated wood block and a pair of grooves 5 are formed in the top surface, these grooves being spaced by the same distance as the grooves 2 in the knee portion 1. Plates 6 of synthetic resin bonded plywood inset in the shin portion define the inner sides of the grooves 5.

Two holes 7 extend transversely through the knee portion 1 and two through the shin portion 4, the axes of these four holes being parallel to one another and at right angles to the grooves 2, 5 respectively. Each hole 7 is lined with a bush 8 throughout its length except where it crosses the grooves.

Bearings for front or rear links 9, 10 are mounted in these holes 7. These bearings are formed by a central distance piece 11, a counter-sunk bearing piece 12 and a threaded bearing piece 13 connected by a counter-sunk headed screw 14. The adjacent ends of the distance piece 11, and the two bearing pieces 12 and 13 are of reduced diameter to accommodate links which are clamped to the bearing members by the screw 14. Washers 15 of nylon are provided at the inner ends of the bearing pieces 12 and 13.

The knee portion 1 and the shin portion 4 are connected by a pair of front links 9 secured at their ends to the bearing provided by the distance piece 11 and the bearing surfaces 12, 13 and by a pair of longer rear links 10 similarly secured at their ends to the bearings.

The position of the holes 7 and the effective length of the links 9, 10 are such that the instantaneous center of rotation of the articulation (that is the intersection point of a line drawn through the pivot points of a front link and a line drawn through the pivot points of a forward link) lies upon an ascending curve for a predetermined angle of relative rotation between the knee and shin portions and thereafter drops. As a result there is a resistance to flexure during this first rotation followed by a relatively free movement to a fully flexed position.

The front links 9 are cranked and buffer stops 16 are provided at the bottom of the grooves against which the links abut when the leg is in its fully extended position. In the fully flexed position, the rear surface of the knee portion abuts against a buffer stop on the top surface of the shin portion between the grooves 5.

A recess 18 is formed in the rear of the knee portion between the grooves 2 and a brake block 19 of nylon or the like is secured in this recess. This block 19 surrounds the distance piece 11 of the rear bearing and is formed with a slot 20. A screw 21 extends across this slot so that by screwing up the screw 21 the brake block may be clamped more firmly around the distance piece 11 and the friction therebetween increased. The force required to flex the joint can thus be adjusted by adjustment of the screw 21.

It will be understood that the invention is not restricted to the details of the referred form described by way of example which may be modified without departure from the scope of the accompanying claims.

I claim:

1. An artificial leg comprising a solid shaped knee portion, a solid shaped shin portion, confronting surfaces of each of said portions being each formed with a pair of transverse grooves, a pair of front links each engaged in said grooves and pivotally connected at their opposite ends to said knee portion and said shin portion respectively, and a pair of rear links each engaged in said grooves and pivotally connected at their opposite ends to said knee portion and said shin portion respectively, said front links having an effective length less than that of said rear links, and said pivotal connections of said front and rear links to said knee and shin portion being positioned to form an articulation of which the instantaneous center of rotation lies upon an ascending curve for a predetermined angle of relative rotation between said knee portion and said shin portion from the fully extended position thereof, each said pivotal connection comprising a tubular central distance piece having a portion of reduced diameter at each end thereof, a first tubular bearing piece at one end of said distance piece and of reduced diameter adjacent said distance piece, a second internally threaded bearing piece at the other end of said distance piece and of reduced diameter adjacent said distance piece, the ends of said links being engaged over said adjacent portions of reduced diameter, and a screw passing through said first bearing piece and said distance piece and threaded into said second bearing piece to clamp the links between said central piece and said first and second bearing piece.

2. An artificial leg as defined in claim 1, wherein said knee portion and said shin portion are each shaped from a block of laminated wood and plates of synthetic resin bonded plywood inset therein define an inner side of said grooves.

3. An artificial leg as defined in claim 1 including a plastics block surrounding said distance piece, and a screw passing through said block and operable to adjustably clamp said plastics block around said distance piece whereby the effort required to flex the knee may be adjustably controlled.

4. An artificial leg as defined in claim 1, wherein said front links are cranked and including buffer stops at the bottom of the grooves in the knee portion abutted by said cranked links in the extended position of the leg.

5. An artificial leg comprising a solid shaped knee portion, a solid shaped shin portion, confronting surfaces of each of said portions being each formed with a pair of transverse grooves, a pair of front links each engaged in said grooves and pivotally connected at their opposite ends to said knee portion and said shin portion respectively, and a pair of rear links each engaged in said grooves and pivotally connected at their opposite ends to said knee portion and said shin portion respectively, said front links having an effective length less than that of said rear links, and said pivotal connections of said front and rear links to said knee and shin portion being positioned to form an articulation of which the instantaneous center of rotation lies upon an ascending curve for a predetermined angle of relative rotation between said knee portion and said shin portion from the fully extended position thereof, said pivotal connections comprising a tubular distance piece between the ends of the links in the grooves, screws passing through said distance pieces and extending beyond each end thereof into the knee and shin portions respectively, and clamping means accessible for adjustment from outside said knee and shin portions and comprising a brake lock for selectively clamping at least one of said distance pieces between said links.

* * * * *